(12) United States Patent
Leze

(10) Patent No.: US 7,563,914 B2
(45) Date of Patent: Jul. 21, 2009

(54) METHOD FOR PREPARING PACLITAXEL

(75) Inventor: Antoine Paul Gaston Leze, La Milesse (FR)

(73) Assignee: Seripharm, Le Mans (FR)

( * ) Notice: Subject to any disclaimer, the term of this patent is extended or adjusted under 35 U.S.C. 154(b) by 0 days.

(21) Appl. No.: 11/816,857

(22) PCT Filed: Feb. 21, 2006

(86) PCT No.: PCT/FR2006/000387

§ 371 (c)(1),
(2), (4) Date: Apr. 3, 2008

(87) PCT Pub. No.: WO2006/090057

PCT Pub. Date: Aug. 31, 2006

(65) Prior Publication Data

US 2008/0207929 A1    Aug. 28, 2008

(30) Foreign Application Priority Data

Feb. 23, 2005   (FR) .................................. 05 01838

(51) Int. Cl.
*C07D 305/00* (2006.01)
(52) U.S. Cl. .................................... 549/510
(58) Field of Classification Search .................. 549/510
See application file for complete search history.

(56) References Cited

U.S. PATENT DOCUMENTS

| 5,637,723 | A | 6/1997 | Commercon et al. |
| 6,184,395 | B1 | 2/2001 | Singh et al. |
| 6,222,053 | B1 | 4/2001 | Zamir et al. |
| 6,365,750 | B1 | 4/2002 | Thottathil et al. |
| 2002/0161238 | A1 | 10/2002 | Thottathil et al. |
| 2007/0027330 | A1 | 2/2007 | Naidu et al. |

FOREIGN PATENT DOCUMENTS

| WO | WO 94/07878 A | 4/1994 |
| WO | WO 00/69840 A | 11/2000 |
| WO | WO 2006/004708 A | 1/2006 |

OTHER PUBLICATIONS

Kingston D. et al., Synthesis of Taxol From Baccatin III, Elsevier, 1994, 4483-4484, vol. 35, No. 26, Amsterdam.
Holton R. A. et al., Selective Protection of the C(7) and C(10) Hydroxyl Groups in 10-Deacetyl Baccatin III, Tetrahedron Letters, Apr. 7, 1998, Elsevier, pp. 2883-2886, Amsterdam, NL.

*Primary Examiner*—Janet L. Andres
*Assistant Examiner*—Raymond Covington
(74) *Attorney, Agent, or Firm*—Millen, White, Zelano, Branigan, P.C.

(57) ABSTRACT

The invention concerns a method for preparing paclitaxel characterized in that it consists in starting with 10-deacetyl-baccatine in accordance with a "one-pot" reaction including the following three steps: a) protecting the hydroxy radical in position 7 of 10-deacetylbaccatine with a silylated radical, then b) acetylating the hydroxy radical in position 10, c) optionally crystallizing the resulting baccatine III derivative, followed by condensation of (4S,5R)-3-N-benzoyl-2RS-methoxy-4-phenyl-1,3-oxazolidine-5-carboxylic acid, by esterifying in position 13 the acetylated 10-baccatine III derivative previously obtained, then opening the oxazolidine of the cyclic side chain and simultaneously releasing the hydroxy radical in position 7.

5 Claims, No Drawings

METHOD FOR PREPARING PACLITAXEL

The present invention relates to a process for preparing paclitaxel from 10-deacetyl baccatin (10-DAB).

Patent application WO 94/07878 described the process which consists in preparing taxane derivatives, in particular paclitaxel, from protected 10-DAB or baccatin III, involving intermediately a baccatin III derivative comprising an oxazolidine cyclic chain, and then opening this chain. However, the various steps, in particular the prior steps of preparation of protected 10-DAB or of baccatin III, are not specifically described and had never been optimized for the purpose of an effective industrial implementation, which did not make it possible to achieve results as satisfactory as desired for industrial application on a greater scale.

Patent application WO 2006/004708 described the process for protecting a taxane of formula:

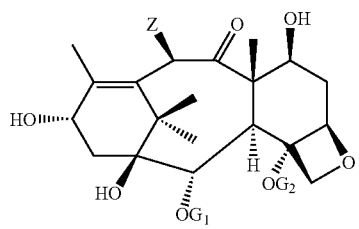

in which Z is —OH or a protected —OH, and $G_1$ and $G_2$ are identical or different and independently represent a hydroxyl-protecting group, the process comprising: protection of the free hydroxyls in the C-7 position and/or in the C-10 position of the taxane, and condensation of a side chain on the hydroxyl in the C-13 position of the taxane so as to prepare a C-13 protected intermediate taxane, and in which the protection and condensation steps are characterized in that, in a "one-pot" reaction, the taxane is combined with a base, a suitable hydroxyl-protecting agent and a side chain precursor, and in which the side chain precursor is a β-lactam, an oxazolidine or an oxazoline.

According to the invention, it has now been found that paclitaxel can be advantageously prepared from 10-deacetyl baccatin according to a "one-pot" reaction involving the following 3 successive steps:

a) protection of the hydroxyl radical in the 7-position of the 10-DAB, with a silylated radical, then b) acetylation of the hydroxyl radical in the 10-position, c) optionally, crystallization of the baccatin III derivative obtained, followed by condensation of (4S,5R)-3-N-benzoyl-2RS-methoxy-4-phenyl-1,3-oxazolidine-5-carboxylic acid of formula:

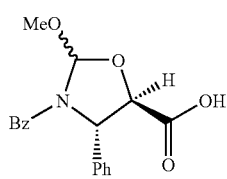

by esterification in the 13-position of the 10-acetylated derivative of baccatin III obtained above, of general formula:

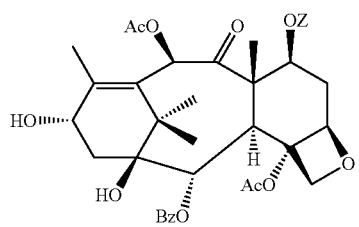

in which Z is a silylated protective radical, so as to obtain a derivative of general formula:

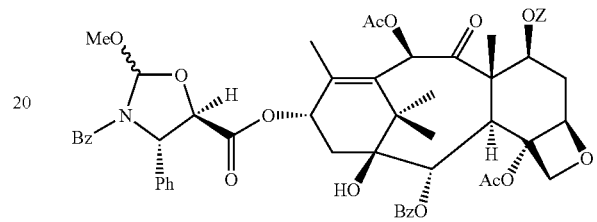

in which Z is a silylated protective radical, and then opening of the oxazolidine of the cyclic side chain and simultaneous deprotection of the hydroxyl radical in the 7-position, from its protective radical, and optional purification of the paclitaxel obtained.

The protective radical Z is chosen from silylated protective radicals normally used in taxane chemistry and whose introduction and elimination does not impair the rest of the molecule. In particular, the radical protecting the hydroxyl in the 7-position can be chosen from trialkylsilyl, dialkylarylsilyl, alkyldiarylsilyl or triarylsilyl groups in which the alkyl radicals contain 1 to 4 carbons in a straight or branched chain, and aryl is preferably phenyl, for example triethylsilyl or trimethylsilyl radicals, preferably triethylsilyl radicals.

The protection of the hydroxyl radical in the 7-position of the 10-DAB, with a silylated radical, is advantageously carried out by the action of triethylsilyl chloride in the presence of pyridine (anhydrous pyridine) according to the method described in European patent EP336840, or in the presence of dimethylamino-4-pyridine in a solvent such as dichloromethane according to the method described in international application WO 94/14787. The reaction is carried out at a temperature of between 0 and 10° C., preferably at a temperature of between 5 and 10° C.

The acetylation b) of the silylated 10-DAB is carried out by the action of acetyl chloride or acetic anhydride under the conditions described in European patent EP336840. Preferably, the process is carried out by adding acetic anhydride in pyridine, at a temperature of between 0 and 25° C., preferably at a temperature in the region of 20° C.

When it is desired to purify the acetylated derivative obtained, crystallization of the baccatin III derivative protected in the 7-position is advantageously carried out from a 50/50, by volume methanol/water mixture. Preferably, 7-triethylsilyloxy-baccatin III is used and the process is carried out at a temperature of between 0 and 30° C., the temperature then being maintained at approximately 10° C.

It is understood that the 3 steps of protection of the hydroxyl radical in the 7-position, of acetylation in the 10-position and, optionally, of crystallization of the baccatin III derivative protected in the 7-position are carried out without isolation of the intermediate products formed.

The esterification of the 10-acetylated derivative of baccatin III, of general formula:

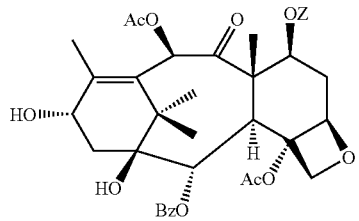

in which Z is a silylated protective radical, with (4S,5R)-3-N-benzoyl-2RS-methoxy-4-phenyl-1,3-oxazolidine-5-carboxylic acid, is carried out in the presence of a condensation agent such as, for example, a carbodiimide (dicyclohexylcarbodiimide, for example) and of a nitrogenous base such as an aminopyridine (4-dimethylaminopyridine, 4-pyrrolidinopyridine). The reaction is carried out in an organic solvent such as an ether, an ester (ethyl acetate, for example), a nitrile or an aliphatic or aromatic hydrocarbon, at a temperature of between −10 and 90° C., preferably at a temperature of between 10 and 30° C., and more preferably between 20 and 25° C. Advantageously, the ester thus obtained is crystallized in the presence of methanol.

The opening of the oxazolidine of the cyclic side chain and simultaneous deprotection of the hydroxyl radical in the 7-position are carried out in an organic solvent such as an ester (ethyl acetate, for example) or an alcohol (ethanol or methanol, for example) or in a mixture of these solvents, for example ethyl acetate/ethanol mixture, by the addition of an acid such as, for example, a halogenated acid, for example hydrochloric acid, at a temperature of between 35 and 55° C., preferably at a temperature of between 40 and 50° C., and then by addition of water. Preferably, the process is carried out under an inert atmosphere. The crude paclitaxel thus obtained is purified by chromatography and crystallization.

Operating conditions are also described in international application WO 94/07878.

The following example illustrates the present invention.

EXAMPLE 1

7-O-Triethylsilyl-baccatin III

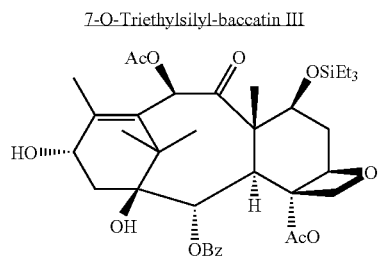

0.42 g (2.79 mmol) of chlorotriethylsilane is added, in 30 min, to a solution, stirred at 5° C. under an inert atmosphere, of 1 g (1.84 mmol) of 10-deacetyl baccatin III in 2 ml of anhydrous pyridine. After reaction for 24 hours at 5° C., 0.37 g (3.62 mmol) of acetic anhydride is added in 30 minutes and the reaction mixture is then brought back to ambient temperature. After reaction for 22 h, 5 ml of a mixture of methanol/water (50/50) are added in 30 minutes. The suspension is kept stirring for 30 minutes and is then filtered through sintered glass.

After drying, 1.09 g of the compound mentioned above in the title are thus obtained, in the form of a white solid (yield=85%).

The compound obtained has the following characteristics;

$^1$H NMR 400 MHz (CDCl$_3$) (δ ppm): 8.11 (2H, d, J=7.1 Hz); 7.6 (1H, t, J=7.4 Hz); 7.48 (2H, t, J=7.7 Hz); 6.46 (1H, s); 5.63 (1H, d, J=7 Hz); 4.96 (1H, d, J=8.1 Hz); 4.83 (1H, m); 4.49 (1H, dd, J=10.4 and 6.7 Hz); 4.31 and 4.15 (2H, 2d, J=8.3 Hz); 3.38 (1H, d, J=7Hz); 2.53 (1H, m); 2.29 (3H, s); 2.27 (2H, m); 2.19 (3H, d, J=0.8 Hz); 2.18 (3H, s); 2.12 (1H, d); 1.88 (1H, m); 1.68 (3H, s); 1.65 (1H, s); 1.2 (3H, s); 1.04 (3H, s); 0.92 (9H, t); 0.59 (5H, m).

EXAMPLE 2

13-O-[[(4S,5R)-3-N-benzoyl-4-phenyloxazolidin-2RS-methoxy-5-yl]carbonyl]-7-O-triethylsilyl-baccatin III

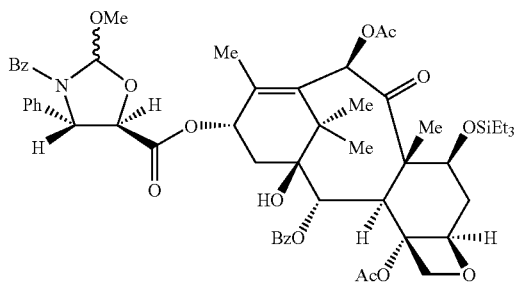

1 g (1.43 mmol) of 7-O-triethylsilylbaccatin III is added to a solution, stirred under an inert atmosphere at ambient temperature, of 0.58 g (1.77 mmol) of (4S,5R)-3-N-benzoyl-4-phenyloxazolidin-2RS-methoxy-5-carboxylic acid in 6.5 ml of ethyl acetate. A solution of 0.73 g (3.54 mmol) of dicyclohexylcarbodiimide in 1 ml of ethyl acetate and 0.02 g (0.16 mmol) of 4-dimethylaminopyridine are added. After reaction for 1 hour, the insoluble material is removed by filtration and the organic phase is concentrated under reduced pressure.

1.36 g of the compound mentioned above in the title are obtained, in the form of a yellowish residue (yield=95%).

The compound obtained has the following characteristics:

$^1$H NMR 400 MHz (CDCl$_3$) (δ ppm): 8.13 (2H, d, J=7.3 Hz); 7.75 (2H, d, J=7.3 Hz); 7.61 (1H, t, J=7.4 Hz); 7.50 (5H, m); 7.41 (5H, m); 7.05 (1H, d, J=9.0); 6.43 (1H, s); 6.19 (1H, t, J=8.6 Hz); 5.80 (1H, dd, J=8.9 and 2.4 Hz); 5.69 (1H, d, J=7 Hz); 4.92 (1H, d, J=8.1 Hz); 4.80 (1H, 4, J=2.4 Hz); 4.44 (1H, J=10.4 and 6.7 Hz); 4.30 and 4.19 (2H, 2d, J=8.4 Hz); 3.80 (1H, d, J=7Hz); 3.63 (1H, s); 2.52 (1H, m); 2.38 (3H, s); 2.31 (2H, m); 2.18 (3H, s); 1.91 (3H, d, J=0.6 Hz); 1.88 (1H, m); 1.70 (3H, s); 1.23 (3H, s); 1.18 (3H, s); 0.97 (6H, t, J=8.0 Hz); 0.92 (3H, t, J=8.0 Hz); 0.59 (6H, m).

EXAMPLE 3

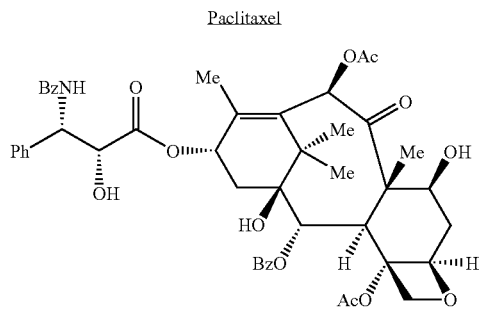
Paclitaxel 2 ml (3 mmol) of a 1.5N aqueous solution of HCl are added to a stirred solution, heated to 45° C. under an inert atmosphere, of 1 g (1 mmol) of 13-O-[[(4S,5R)-3-N-benzoyl-4-phenyloxazolidin-2RS-methoxy-5-yl]carbonyl]-7-O-triethylsilyl-baccatin III in a mixture of 8 ml of ethyl acetate and 4 ml of ethanol. After reaction for 1 hour, 2 ml of water are added and the reaction mixture is stirred for a further 3 hours at 45° C. After the addition of 16 ml of ethyl acetate, the organic phase is washed with 11 ml of a saturated aqueous solution of sodium hydrogen carbonate and then with 11 ml of a saturated aqueous solution of sodium chloride, and concentrated under reduced pressure.

After chromatography of the crude product on silica gel (10 µm) (eluent: cyclohexane/ethyl acetate, 5/5) and crystallization from a mixture of ethanol and water (25/75), 0.65 g of paclitaxel is thus isolated in the crystalline state (yield=80%.

What is claimed is:

1. A process for preparing paclitaxel, comprising reacting 10-deacetyl baccatin in a "one-pot" reaction, successively:
   a) protecting the hydroxyl radical in the 7-position of the 10-DAB, with a silylated radical, then
   b) acetylating the hydroxyl radical in the 10-position,
   c) optionally, crystallizing a baccatin III compound obtained, followed by condensing (4S,5R)-3-N-benzoyl-2RS-methoxy-4-phenyl-1,3-oxazolidine-5-carboxylic acid of formula:

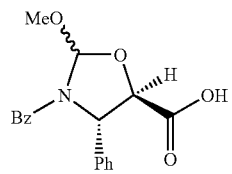

by esterification in the 13-position of the 10-acetylated compound of baccatin III obtained above, of formula:

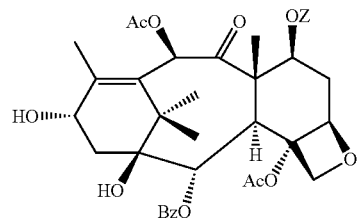

in which Z is a silylated protective radical, so as to obtain a compound of formula:

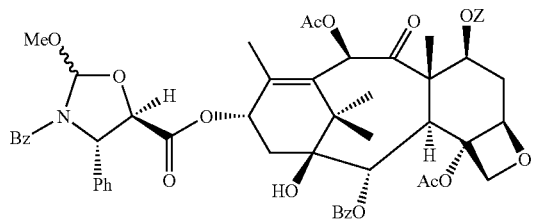

in which Z is a silylated protective radical, and then opening of the oxazolidine of the cyclic side chain and simultaneous deprotection of the hydroxyl radical in the 7-position, from its protective radical, and optional purification of the paclitaxel obtained.

2. The process as claimed in claim 1, wherein the silylated protective group is trialkylsilyl, dialkylarylsilyl, alkyldiarylsilyl or triarylsilyl groups in which the alkyl radicals contain 1 to 4 carbons in a straight or branched chain, and aryl represents phenyl.

3. The process as claimed in claim 2, wherein the silylated protective radical is triethylsilyl or trimethylsilyl radicals.

4. The process as claimed in claim 1, wherein the baccatin III compound protected in the 7-position is crystallized from a methanol/water mixture.

5. The process as claimed in claim 4, wherein the baccatin III compound protected in the 7-position is 7-triethylsilyloxy-baccatin III.

* * * * *